United States Patent [19]

Saito et al.

[11] Patent Number: 5,707,854
[45] Date of Patent: *Jan. 13, 1998

[54] **LACTIC ACID BACTERIA OF THE *GENUS LACTOBACILLUS***

[75] Inventors: Yoshio Saito, Hachioji; Jun Mizutani, Sagamihara, both of Japan

[73] Assignee: Calpis Food Industry Co., Ltd., Tokyo, Japan

[*] Notice: The term of this patent shall not extend beyond the expiration date of Pat. No. 5,516,684.

[21] Appl. No.: 579,573

[22] Filed: Dec. 27, 1995

Related U.S. Application Data

[63] Continuation of Ser. No. 399,209, Mar. 6, 1995, Pat. No. 5,516,684.

[30] Foreign Application Priority Data

Mar. 11, 1994 [JP] Japan .................. 6-040921

[51] Int. Cl.$^6$ .................. C12N 1/20; C12N 1/04
[52] U.S. Cl. .................. 435/252.9; 435/260
[58] Field of Search .................. 435/252.9, 854, 435/260

[56] References Cited

U.S. PATENT DOCUMENTS

| | | | |
|---|---|---|---|
| 2,442,502 | 6/1948 | Meijlho | 435/252.9 |
| 5,032,399 | 7/1991 | Gorbach et al. | 424/93 |
| 5,179,020 | 1/1993 | Heiman et al. | 435/252.9 |
| 5,354,687 | 10/1994 | Hashimoto et al. | 435/252.9 |
| 5,372,810 | 12/1994 | Onishi et al. | 424/93.4 |

FOREIGN PATENT DOCUMENTS 0113215  7/1984  European Pat. Off. ......... 435/2529

OTHER PUBLICATIONS

Feighner et al. (1987) *Applied Envir. Microbiology*, pp. 331–336 "Subtherapeutic Levels of Antibiotics . . . ".

Bergey's Manual, 8th Ed. pp. 578, 581–583, 1978.

King et al., *American Gastroenterology*, Assci, 76:1035–1055, 1979.

*Primary Examiner*—John W. Rollins
*Assistant Examiner*—Deborah K. Ware
*Attorney, Agent, or Firm*—Darby & Darby

[57] ABSTRACT

Lactic acid bacteria of the genus Lactobacillus do not exhibit deconjugation of bile acids and inhibition of nutrient absorption, and exhibit lowering of cholesterol in blood and liver. The particular species of the genus Lactobacillus exhibiting these characteristics is *Lactobacillus acidophilus*. Furthermore, the strain *Lactobacillus acidophilus* CL-0062 has been internationally deposited under accession number FERM BP-4980.

1 Claim, No Drawings

LACTIC ACID BACTERIA OF THE *GENUS LACTOBACILLUS*

This is a continuation of application Ser. No. 08/399,209, filed Mar. 6, 1995, now U.S. Pat. No. 5,516,684.

BACKGROUND OF THE INVENTION

This invention relates to novel lactic acid bacteria of the genus Lactobacillus. More particularly, it relates to novel lactic acid bacteria of the genus Lactobacillus capable of lowering cholesterol in blood and liver without exhibiting the properties proper to known lactic acid bacteria of the genus Lactobacillus, that is without exhibiting deconjugation of conjugated bile acids, which are believed to raise the risk of cancer of large intestine and inhibition of absorption of lipid nutrients, such as essential fatty acids or fat-soluble vitamins.

There have so far been made a number of reports on the lactic acid bacteria of the genus Lactobacillus showing the lowering of cholesterol in blood. For example, it was reported by Grunewald in J. of Food Science 47: pages 2078 to 2079 (1982) that the serum cholesterol level could be significantly decreased ($p<0.05$) when rats were given feeds containing 10% of fermented milk by *Lactobacillus acidophilus* for four weeks. It was also reported by Gilliland et al. in Applied and Environmental Microbiology 49: pages 377 to 381 (1985) that the rise in the serum cholesterol level in pigs fed with high cholesterol feeds could be significantly inhibited when feeding the pigs with *Lactobacillus acidophilus* which was derived from the intestinal tract of the pigs and which had the ability of growth in the presence of bile acids in vitro and the ability of metabolizing cholesterol. In addition, it was reported by Suzuki et al. in Animal Science and Technology 62 (6): pages 565 to 571 (1987), that the effect in suppressing the rise in serum cholesterol level was recognized in rats given the *Lactobacillus acidophilus*-fermented milk together with high cholesterol feed for 12 days, and that the lactic acid bacteria decreased the absorption of cholesterol micelle from the intestinal tract.

On the other hand, bile acids are synthesized in vivo in the liver from cholesterol and are contained in bile. They are useful in digestion and absorption of lipids and are usually bound by amido-linkage with glycine or taurine to give a conjugation form so as to exist as taurocholic acid or glycocholic acid. If the conjugated bile acids are deconjugated in the intestines, they become hardly susceptible to absorption in the lower intestine. If the bile acids are converted in the large intestine by enterobacteria into secondary bile acids, they exhibit harmful carcinogenicity; Gilliland et al. reported in Applied and Environmental Microbiology 33: pages 15 to 18 (1977) that *Lactobacillus acidophilus* isolated from human intestinal tract unexceptionally exhibited deconjugation activity of bile acids.

In keeping up with changes in our daily diet after the European and American type diet and in our living style, the heart disease recently has come to rank highly in Japan among the causes of death. While it is encouraged to decrease the ingestion of animal fats containing a large quantity of cholesterol that causes arteriosclerosis, to increase chances of bodily exercises in our daily life or to refrain from smoking as danger factors, as much as possible, it is usually difficult to change our long nurtured life custom. Although pharmaceuticals effective for hyperglycemia have been developed, they are frequently susceptible to dangerous side effects. Recently, attention is directed to diet therapy which is effective for less serious cases of hyperglycemia. Under such situation, there has been desired an ingredient among highly palatable and readily ingestible foods capable of preventing hyperglycemia as the main cause of the heart disease.

Some of the lactic acid bacteria have been reported to decrease the serum cholesterol, as previously discussed. Although the detailed operating mechanism is not known, such decrease in serum cholesterol is felt to be ascribable to cholesterol adsorption (Bottazzi et al., Annual Microbiology 36: pages 1 to 6, (1986)), to adsorption of bile acids, or to deconjugation activity of bile acids such as taurocholic acid or glycocholic acid by lactic acid (Gilliland et al. (1977)). However, it has also been pointed out that such bile acid deconjugation has a latent risk that free cholic acid is produced to inhibit the cholesterol absorbtion of the conjugated bile acids and to inhibit absorption of nutrients such as fats or fat-soluble vitamins (Rambaud et al., Microbiology Reviews 12: pages 207 to 220 (1993)). For example, deconjugation of bile acids in the upper part of the small intestine is clinically well known to produce insufficient lipid absorption and diarrhea (King and Toskes Gastroenterology 76: pages 1035 to 1055 (1979)). In raising the livestock, germ free animals gain body weight more significantly than usual animals having enterobacteria (Coats et al., British J. of Nutrition 13: pages 205 to 212, 1959). Suppression of deconjugation activity of bile acids by enterobacteria leads to improved growth of animals (Feighner and Dashkevicz, Applied Environmental Microbiology 53: pages 331 to 336 (1987)) so that the deconjugation activity of bile acids is thought to have a crucial role in digestion and absorption of nutrients. On the other hand, the deconjugated bile acids are hardly re-absorbed in the ileum and hence are liable to be transferred to the large intestine where it is converted to secondary bile acids which are promotors of cancer. Thus, the deconjugated bile acids are thought to increase the risk of cancer in large intestine (Hill, Mutation Research 238: pages 313 to 320 (1990)).

However, there lacks up to now a report on means for creating lactic acid bacteria of the genus Lactobacillus which exhibit the lowering of cholesterol in blood without exhibiting the deconjugation of bile acids and the inhibition of absorption of nutrients, or a report on such lactic acid bacteria of the genus Lactobacillus per se.

SUMMARY OF THE INVENTION

It is an object of the present invention to provide novel lactic acid bacteria of the genus Lactobacillus which exhibits lowering of cholesterol in blood without exhibiting deconjugation of bile acids, thereby not forming secondary bile acids and without exhibiting inhibition of nutrient absorption.

These and other objects of the present invention will become clear from the following description.

According to the present invention, there is provided lactic acid bacteria of the genus Lactobacillus wherein the bacteria do not exhibit deconjugation of bile acids and inhibition of nutrient absorption, and exhibit lowering of cholesterol in blood and liver.

PREFERRED EMBODIMENTS OF THE INVENTION

The present invention will be explained in more detail hereinbelow.

The lactic acid bacteria of the genus Lactobacillus according to the present invention is in no way different from well-known lactic acid bacteria as to bacteriological properties, namely gram positive, rod shape, non-mobility, negative catalase, facultative anaerobic properties, optimum growth temperature of 30° to 40° C., no growth at 15° C. and formation of DL-lactic acid, except that the bacteria of the present invention exhibit the characteristics different from the well known lactic acid bacteria, that is lowering of cholesterol in blood and liver while they do not exhibit deconjugation of bile acids nor inhibition of nutrient absorption.

Such lactic acid bacteria of the genus Lactobacillus according to the present invention preferably belong to the *Lactobacillus acidophilus* and may preferably be enumerated by lactic acid bacteria having the above-mentioned properties. Specific examples include *Lactobacillus acidophilus* CL-92 and *Lactobacillus acidophilus* CL-0062 deposited before the NATIONAL INSTITUTE OF BIOSCIENCE AND HUMAN-TECHNOLOGY, AGENCY OF INDUSTRIAL SCIENCE AND TECHNOLOGY, 1-3, Higashi 1 chrome Tsukuba-shi Ibaraki-ken, under the deposit numbers of FERM-P-14205 (International Deposit No. BP-4981) and FERM-P-14204 (International Deposit No. BP-4980), respectively on Mar. 3, 1994.

The aforementioned *Lactobacillus acidophilus* CL-92 having the international deposit number of FERM-BP-4981 exhibits lowering of cholesterol in blood and liver without exhibiting deconjugation of bile acids and inhibition of nutrient absorption, and has the following bacteriological properties:

Morphological Properties;
1) Morphology, rod shape;
2) Mobility, none;
3) Spore formation, none;
4) Gram stain, positive.

Physiological Properties;
1) Catalase, negative;
2) Indole production, negative;
3) Nitrate reduction, negative;
4) Resistanse against oxygen, facultative anaerobic;
5) Growth at 15° C., none;
6) Formation of DL-lactic acid from glucose by homolactic acid fermentation without formation of gases;
7) Formation of acids from carbohydrates; glucose, (+); melibiose, (−); lactose, (+); raffinose, (+); mannose, (+); mannitol, (−); fructose, (+); sorbitol, (−); galactose, (+); esculin, (+); sucrose, (+); salicin, (+); arabinose, (−); N-acetyl glucosamine, (+); maltose, (+); amygdalin, (+); xylose, (−); gentiobiose, (+); rhamnose, (−); melezitose, (−); cellobiose, (+); dextrin, (−); trehalose, (+); starch, (−).

On the other hand, the aforementioned *Lactobacillus acidophilus* CL-0062 having the international deposit number of FERM-BP-4980 exhibits the following bacteriological properties:

Morphological Properties;
1) Morphology, rod shape;
2) Mobility, none;
3) Spore formation, none;
4) Gram stain, positive.

Physiological Properties;
1) Catalase, negative;
2) Indole production, negative;
3) Nitrate reduction, negative;
4) Resistanse against oxygen, facultative anaerobic;
5) Growth at 15° C., none;
6) Formation of DL-lactic acid from glucose by homolactic acid fermentation without formation of gases;
7) Formation of acids from carbohydrates; glucose, (+); melibiose, (+); lactose, (+); raffinose, (+); mannose, (+); mannitol, (−); fructose, (+); sorbitol, (−); galactose, (+); esculin, (+); sucrose, (+); salicin, (+); arabinose, (−); N-acetyl glucosamine, (+); maltose, (+); amygdalin, (+); xylose, (−); gentiobiose, (+); rhamnose, (−); melezitose, (−); cellobiose, (+); dextrin, (+); trehalose, (+); starch, (−).

The lactic acid bacteria of the genus Lactobacillus according to the present invention is obtained, e.g. by screening by the following tests (1) to (6).

(1) Isolation/Identification Test

A test substance containing lactic acid bacteria, such as fresh human feces, is cultivated and the resulting colonies are observed under a microscope by gram staining and identified as being gram-positive rod-shaped lactic acid bacteria. The strains identified as being of the genus Lactobacillus, such as *Lactobacillus acidophilus* are isolated by tests for checking acid formation from carbohydrates, optical activity with respect to lactic acid, growth at 15° C., gas formation or negative catalase.

(2) Cholesterol Adsorption Test

The lactic acid strains are cultured and collected by centrifugal separation. The collected bacteria are dispersed in a phosphoric acid buffer admixed with a cholesterol source, e.g., PPLO (BACT PPLO SERUM FRACTION) prepared by DIFCO LABORATORIES, and incubated. The cholesterol concentration of the supernatant resulting from centrifugal separation is measured and the percentage of cholesterol adsorbed by the lactic acid bacteria is determined in order to select the strains having the cholesterol adsorption percentage in excess of 20%.

(3) Bile Acid Adsorption Test

The lactic acid strains are freeze-dried, dispersed in a phosphoric acid buffer containing taurocholic acid and incubated. The bile acid concentration of the supernatant produced by centrifugal separation is measured and the percentage of the bile acids adsorbed by the lactic acid bacteria is determined for each strain in order to select and separate the strains having bile acid adsorption percentages of not lower than 50%.

(4) Test on Deconjugation of Bile Acids

The selected bacteria strains are cultured and centrifuged to produce bacteria which are then re-dispersed in a phosphoric acid buffer of the same volume containing taurocholic acid or glycocholic acid as that of the culture liquid and incubated. The bacteria are then removed by centrifugal separation and the supernatant is analyzed by a silica gel G thin layer chromatography or the like in order to measure the amount of formation of cholic acid. Such analysis may be conducted by coloration with a coloring agent using a 2:1:1:1 solution of isooctane:isopropyl ether:glacial acetic acid:isopropanol as a developing solvent. Those bacteria strains in which no spot was observed at the cholic acid position are selected.

The lactic acid bacteria through the above in vitro screening are then subjected to animal teats (5) and (8).

(5) Test on Serum and Liver Cholesterol

Test groups of animals under test, such as SD rats, are inoculated with strains of lactic acid bacteria selected by the in vitro tests up to (4) above and containing cholesterol and sodium cholate, and are fed by free ingestion with purified diet containing freeze-dried powders of cultured fermented milk. The control groups of the animals are fed ad libitum with purified diet containing the same amount of cholesterol and sodium cholate as that for the teat groups and also containing non-fermented skim milk powders. The animals thus fed for 10 days are dissected and blood is sampled from the caudal abdominal large vein while at the same time the livers are taken out in order to measure the cholesterol in serum and in liver. The bacteria strains with the greater lowering ability in cholesterol are selected.

(8) Growth Test on Animals by Administration of Fermented Milk with Lactic Acid Bacteria Test groups of animals under test, such as SD rats, are inoculated with lactic acid bacteria containing cholesterol and sodium cholate, as selected at (5), and are given purified diet containing freeze-dried powders of cultured fermented milk ad libitum. The control groups were given purified diet containing non-fermented skim milk powder and the same amounts of cholesterol and sodium cholate as those for the test groups for free ingestion. The animals are kept for 30 days and the amounts of feed and the gain in body weight are measured. Those lactic acid bacteria which show no difference in body weight or the feed efficiency nor inhibition of nutrient absorption are selected and separated.

By performing the screening of (1) to (6), the desired lactic acid bacteria of the genus Lactobacillus showing the lowering of the cholesterol in blood and liver without exhibiting deconjugation of bile acids or inhibition of nutrient absorption can be obtained. For improving operability and strain selectivity, the screening of (1) to (6) may preferably be carried out in this sequence with or without sequence inversion for (2) and (3).

Using the lactic acid bacteria of the genus Lactobacillus according to the present invention, a starting milk material such as milk or skim milk may be fermented preferably at 15° to 45° C. and more preferably 30° to 40° C. preferably at 10 to 30 hours and more preferably for 15 to 25 hours to prepare fermented milk and suitably admixed with sugar, a sour agent and flavors in order to prepare a milk product, such as fermented milk, yogurt, lactic acid beverages or *acidophilus* milk. Alternatively, the fermented milk may be freeze-dried to give powder. Still alternatively, the powder may be compacted to obtain tablets and orally administered. Lactic acid bacteria for dairy, such as Bifidus bacteria, *Lactobacillus bulgaricus* or *Streptococcus thermophilus*, may also be used in combination, whenever the occasion may demand.

The desired effect in lowering cholesterol in blood and liver may be obtained by ingestion preferably of $10^4$ to $10^{11}$ and more preferably $10^6$ to $10^{11}$ per day in the case of an adult subject in terms of the number of lactic acid bacteria of the genus Lactobacillus of the present invention to be contained in food, beverage or feed.

The lactic acid bacteria of the genus Lactobacillus according to the present invention are novel bacteria having the properties not present in the well known lactic acid bacteria of the genus Lactobacillus. When the bacteria are ingested as viable bacteria, there is no risk of producing harmful secondary bile acids since the bacteria do not exhibit deconjugation of bile acids. In addition, while the well known lactic acid bacteria usually inhibit cholesterol absorption and hence produce inhibition of lipid nutrients, the lactic acid bacteria of the genus Lactobacillus of the present invention exhibit only inhibition of cholesterol absorption, and lowering of cholesterol in blood and liver without exhibiting the inhibition of nutrient absorption. Thus, the lactic acid bacteria of the genus Lactobacillus of the present invention may be utilized for food or beverages, such as dairy products, or feed for livestock.

EXAMPLES OF THE INVENTION

The present invention will be explained with reference to Examples and Referential Examples which are herein given only by way of illustration and are not intended for limiting the invention.

Example 1

The screening by the following tests (1) to (6) was carried out in this sequence in order to isolate the targeted lactic acid bacteria of the genus Lactobacillus. (1) Isolation and Identification of Lactic Acid Bacteria of the genus Lactobacillus 1 g of fresh feces of a healthy human subject was diluted with an anaerobic liquid diluent at a suitable dilution ratio and spread on an LSB flat plate agar medium prepared by BBL MICROBIOLOGY SYSTEMS. The spread mass was cultivated under a slightly aerobic condition at 37° C. for 48 hours. The resulting white-colored colonies were observed under a microscope with gram stain and identified as being lactic acid bacteria. The strains identified as *Lactobacillus acidophilus* were isolated by check tests as to the acid formation from carbohydrates, optical properties with respect to lactic acid, growth at 15° C., gas formation and negative catalase.

(2) Cholesterol Adsorption Test

The strains of lactic acid bacteria were inoculated on an MRS broth admixed with 0.2% sodium thioglycocholate, manufactured by DIFCO LABORATORIES, and cultured at 37° C. for 24 hours. The resulting cultured mass was centrifuged at 5000 rpm for ten minutes. The bacteria were collected and admixed with 0.6 ml of PPLO (BACT PPLO SERUM FRACTION manufactured by DIFCO LABORATORIES). The resulting mixture was dispersed in 3 ml in sum total of 0.1M phosphoric acid buffer containing 1% of Oxgall (BACTO OXGALL) manufactured by DIFCO LABORATORIES. After incubation continuing for three hours, the cholesterol concentration of the supernatant resulting from centrifugation was measured and the percentage of cholesterol adsorbed by the lactic acid bacteria was determined. Almost all of the strains showed the cholesterol adsorption. The strains showing the cholesterol adsorption of 20% or higher, differing from one strain to another, were selected.

(3) Bile Acid Adsorption Test 2.5 mg of the lactic acid bacteria obtained in (2), which were freeze-dried, were dispersed in a 0.2M phosphoric acid buffer containing 0.4 mg of taurocholic acid (pH 7.2) and were incubated at 37° C. for 18 hours. The bile acid concentration of the supernatant resulting from centrifugal separation was measured and the ratio in percentage of bile acids adsorbed by the lactic acid bacteria was determined. Almost all of the strains showed cholesterol adsorption. The strains showing the cholesterol adsorption of 50% or higher, differing from one strain to another, were selected.

(4) Test on Deconjugation of Bile Acids

The strains of lactic acid bacteria obtained in (3), were cultured on an MRS broth at 37° C. for 16 hours. The resulting cultured mass was centrifuged at 5000 rpm for 20 minutes. The bacteria recovered from the centrifugal separation were dispersed in the same volume as the culture liquid, using a 1M phosphoric acid buffer (pH 7.2) containing 10 ml of taurocholic acid or glycocholic acid and were incubated at 37° C. for 2 hours. The supernatant resulting from centrifugal separation at 5000 rpm for 20 minutes for removing the bacteria was analyzed with a silica gel G thin layer chromatography. After development for one hour using a developing solvent (2:1:1:1 solution of isooctane: isopropyl ether: glacial acetic acid: isopropanol), the supernatant was sprayed with a colorant (1:100:2 solution of anisaldehyde:glacial acetic acid: concentrated sulfuric acid) and colored by heating at 125° C. for ten minutes. Analyses were conducted on the strains of CL-92, CL-0062, CL-82, CL-89, CL-68, CA-463, CL-132 and CP-855 of the *Lactobacillus acidophilus*, as selected at (3). Since it was found that the strains of CL-92, CL-0062, CL-82 and CL-89 of *Lactobacillus acidophilus* did not deconjugate bile acids nor produce free cholic acid, these four strains were selected and separated. The results are shown in Table 1.

TABLE 1

Deconjugation of bile acids

| | Deconjugation of bile acids | |
|---|---|---|
| | Taurocholic acid | Glycocholic acid |
| CL-92 | (−) | (−) |
| CL-0062 | (−) | (−) |
| CL-82 | (−) | (−) |
| CL-89 | (−) | (−) |
| CL-68 | (+) | (+) |
| CA-463 | (+) | (+) |
| CL-132 | (+) | (+) |
| CP-855 | (+) | (+) |

After the above-mentioned in vitro screening, the following screening was conducted by the following tests on animals.

(5) Test groups and control groups, each consisting of five male SD rats, four weeks of age, were used. 10% reconstituted skim milk containing 0.5% of cholesterol and 0.12% of sodium cholate, were pasteurized by heating at 95° C. for 20 minutes and inoculated with four *Lactobacillus acidophilus* strains selected at (4), and the resulting mass was cultured at 37° C. for 16 hours to give fermented milk. Purified diet containing 20% of freeze-dried powder of the fermented milk were prepared and given the test groups ad libitum. Each of the feeds contained 2.0×10⁸ viable lactic acid bacteria. The control group animals were given purified diet containing the same amounts of cholesterol and sodium cholate and 20% of non-fermented skim milk powder. The test and control groups were kept for ten days and dissected. Blood was sampled from the hind cava of the abdomen, while the livers were also taken out in order to measure the cholesterol in serum and in liver.

The *Lactobacillus acidophilus* CL-92 and CL-0062 significantly suppressed cholesterol increase as compared to the control groups (p<0.05), as shown in Table 2. Simultaneously, with the *Lactobacillus acidophilus* CL-92 and CL-0062, the arteriosclerosis index indicated by (TC-HDL)/HDL; [(total cholesterol)−(HDL cholesterol)]/ (HDL cholesterol) was lower than that of the control groups, thus showing the therapeutic effects for high cholesterol diseases and to resistance against the arteriosclerosis. Consequently, these two strains were selected. With the CL-82 and CL-89 strains of the Lactobacillus acidophilus, the effect in suppressing increase in cholesterol as compared to that of the control groups was not noticed. The results are shown in Tables 2 and 3.

TABLE 2

Inhibition of cholesterol increase

| | Serum cholesterol value after 10 days | | (TC-HDL) |
|---|---|---|---|
| Section | mg/dl | Control group | /HDL |
| Control group | 250 ± 31 | (100) | 3.48 |
| Strains inhibiting cholesterol increase | | | |
| CL-92 | 192 ± 33* | (79) | 1.14 |
| CL-0062 | 163 ± 32* | (67) | 1.44 |
| Strains not inhibiting chotesterol increase | | | |
| CL-82 | 265 ± 56 | (106) | 2.08 |
| CL-89 | 297 ± 81 | (119) | 3.54 |

*: p < 0.05

TABLE 3

Lowering of liver cholesterol

| | Liver | Cholesterol | Liver cholesterol | |
|---|---|---|---|---|
| Section | weight (g) | concentration (mg/g) | (mg/liver) | Percent relative to control group |
| Control | 15.2 ± 1.1 | 38.6 ± 3.7 | 585.5 ± 44.6 | (100) |
| CL-92 | 15.1 ± 1.4 | 36.8 ± 2.9 | 555.2 ± 32.7 | (94) |
| CL-0062 | 15.2 ± 1.1 | 36.4 ± 3.4 | 548.2 ± 60.1 | (94) |

It was seen from the results of Table 3 that cholesterol accumulated in liver tends to be lowered in the test groups as compared to that in the control groups.

(6) Ten male SD rats were divided into two groups, namely a test group and a control group. The test group was fed ad libitum with purified diet containing 20% of freeze-dried powder of fermented milk produced by pasteurizing 10% reconstituted skim milk containing 0.5% of cholesterol and 0.12% of sodium cholate at 95° for 20 minutes, inoculating the skim milk with *Lactobacillus acidophilus* CL-92 and CL-0062 and culturing the resulting inoculated strains at 37° C. for 16 hours. The diet for each animal contained 2.0×10⁸ lactic acid bacteria. The control group was fed ad libitum with purified diet containing the same amounts of cholesterol and sodium cholate and 20% of non-fermented skim milk. The two groups were kept for 30 days and the amounts of diets and the gain in body weight during the test period were measured. It was seen that no significant difference was noticed in the gain in the body weight or the feed efficiency while no inhibition of nutrient absorption by administration of the fermented milk containing lactic acid bacteria was noticed, as shown in Table 4. The results are shown in Table 4.

TABLE 4

Influence on growth of rat administered with lactic acid bacteria-fermented milk

| Section | Body weight upon starting (g) | Body weight after 30 days (g) | Increased body weight (g) | Amount ingested (g) | Feed efficiency (%) |
|---|---|---|---|---|---|
| Control | 100.5 ± 1.6 | 347.4 ± 14.9 | 246.9 ± 10.2 | 588.1 ± 26.6 | 0.420 ± 0.01 |
| CL-92 | 100.2 ± 1.7 | 350.7 ± 16.1 | 250.5 ± 11.3 | 598.5 ± 30.7 | 0.419 ± 0.01 |
| CL-0062 | 100.0 ± 1.5 | 353.9 ± 19.1 | 253.9 ± 16.3 | 601.5 ± 35.2 | 0.422 ± 0.01 |

Comparative Example 1

Experiments similar to those in (4), (5) and (6) of Example 1 were conducted on the well known *acidophilus* JCM-1132. It was seen from these experiments that, although the effect in suppressing cholesterol increase as compared to the control group was noticed, deconjugation of bile acids and inhibition of nutrient absorption were simultaneously noticed.

Referential Example 1

100 g of 10 wt % reconstituted skim milk were pasteurized in an autoclave at 115° C. for 20 minutes, and the resulting mass was lowered in temperature to 40° C. and inoculated with 3 wt % of a subcultured starter of *Lactobacillus acidophilus* CL-92 (FERM-BP-4981). The resulting mass was cultured at 37° C. for 18 hours so as to be used as a mother starter of the *L. acidophilus*. On the other hand, 100 g of 10 wt % reconstituted skim milk were pasteurized in an autoclave at 115° C. for 20 minutes, and the resulting mass was lowered in temperature to 40° C. and inoculated with 3 wt % of a subcultured starter of *Lactobacillus helveticus* ATCC 15009. The resulting mass was cultured at 37° C. for 18 hours so as to be used as a mother starter of the *L. helveticus*.

100 g of 15 wt % reconstituted skim milk was pasteurized at a temperature of 92° C. and the temperature was then lowered to 32° C. The resulting mass was inoculated with 3 wt % of the mother starter of the *L. acidophilus* and 0.25 wt % of the mother starter of the *L. helveticus* and the resulting mass was cultured at 32° C. for 20 hours so as to be used as a bulk starter.

200 g of 15 wt % reconstituted skim milk was pasteurized at a temperature of 92°±2° C. and the temperature was then lowered to 32° C. The resulting mass was inoculated with 1 wt % of the above bulk starter and cultured at 32° C. for 15 to 18 hours so as to give fermented milk.

150 g of granulated sugar, 150 g of liquid sugar, 250 g of a pectin solution dissolved in 3 wt % of hot purified water at 60° C. or higher and 1500 g of purified water were added to the fermented milk and dissolved therein and agitated. 5 g of 50% lactic acid and 3 g of concocted flavors were added to the resulting mixture and agitated to give a mixed solution as a starting solution. The starting solution was pasteurized at 92° C. and subsequently cooled to 5° C. or lower, after which 200 g of the fermented milk was added and mixed in a germ-free manner. The resulting product was homogenized by a homogenizer (Model 15 15MR-8 TBA, manufactured by APV GAULIN INC.) at a pressure of 150 kg/cm². About 2 kg of lactic acid beverage was produced.

Referential Example 2

10 wt % reconstituted skim milk was pasteurized in an autoclave at 115° C. for 20 minutes, and the resulting mass was lowered in temperature to 40° C. and inoculated with 1 wt % of a subcultured starter of *Lactobacillus delbrueckii bulgaricus* ATCC 11842. The resulting mass was cultured at 37° C. for 18 hours so as to be used as a mother starter of the *L. delbrueckii bulgaricus*. On the other hand, 10 wt % reconstituted skim milk was pasteurized in an autoclave at 115° C. for 20 minutes, and the resulting mass was lowered in temperature to 40° C. and inoculated with 1 wt % of a subcultured starter of the *Streptococcus thermophilus* DSM 20479. The resulting mass was cultured at 37° C. for 18 hours so as to be used as a mother starter of *S. thermophilus*. 10 wt % reconstituted skim milk was pasteurized at 115° C. for 20 minutes in an autoclave and lowered in temperature to 40° C. The resulting mass was inoculated with 3 wt % of a subcultured starter of *Lactobacillus acidophilus* CL-0062 (FERM-BP-4980) and the resulting product was cultured at 37° C. for 18 hours so as to be used as a mother starter for *L. acidophilus*.

10 wt % reconstituted skim milk was pasteurized at 92° C. and subsequently lowered in temperature to 45° C. The resulting mass was inoculated with 1 wt % of the mother starter of *L. delbruedkii bulgaricus* and 2 wt % of the mother starter of *S. thermophilus* and cultured at 42° C. for four hours in order to be used as a yogurt bulk starter. 10 wt % reconstituted skim milk was pasteurized at 92° C. and was lowered in temperature to 40° C. The resulting product was inoculated with 3 wt % of the mother starter of *L. acidophilus* and the resulting mass was cultured at 37° C. for 18 hours so as to be used as a bulk starter for *L. acidophilus*.

150 g of skim milk powders and 50 g of whole milk powders were mixed together, and dissolved and agitated with 800 g of purified water. The resulting solution was pasteurized at 92° C. and the temperature was lowered to 30° C., after which 0.5 wt % of the yogurt bulk starter and 5 wt % of the bulk starter of *L. acidophilus* were added to the solution and cultured for 18 hours so as to give fermented milk.

150 g of granulated sugar and 6 g of pectin were mixed and dissolved in 850 g of hot purified water at 60° to 80° C. while being agitated. 3 g of concocted flavors were added and dissolved in the resulting solution and pasteurized at 92° C. so as to be used as a starting solution.

The starting solution was cooled to 10° C. or lower and admixed aseptically with 1000 g of the fermented milk. The resulting mixture was homogenized at a pressure of 150 g/cm² by a homogenizer (Model 15 15MR-8 TBA, manufactured by APV GAULIN INC.). About 2 kg of yogurt drink was produced.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A biologically pure culture of a *Lactobacillus acidophilus* bacterial strain wherein said *Lactobacillus acidophilus* bacterial strain does not deconjugate taurocholic or glycocholic acid, does not inhibit nutrient absorption, and lowers cholesterol levels in blood and liver of an animal when ingested by said animal.

* * * * *

UNITED STATES PATENT AND TRADEMARK OFFICE
CERTIFICATE OF CORRECTION

PATENT NO. : 5,707,854
DATED : Jan. 13, 1998
INVENTOR(S) : Saito et al.

It is certified that error appears in the above-identified patent and that said Letters Patent is hereby corrected as shown below:

On cover page, item [30], delete "6-040921", and substitute therefor --6-40921--.

On the cover page of the patent, at paragraph [75]:

delete "Hachioji", and substitute therefor --Tokyo--.

Signed and Sealed this

Twenty-first Day of April, 1998

Attest:

BRUCE LEHMAN

*Attesting Officer*    Commissioner of Patents and Trademarks